(12) United States Patent
Chen

(10) Patent No.: US 7,405,188 B2
(45) Date of Patent: Jul. 29, 2008

(54) POLYMERIC GEL SYSTEM AND COMPOSITIONS FOR TREATING KERATIN SUBSTRATES CONTAINING SAME

(75) Inventor: Shih-Ruey T. Chen, Pittsburgh, PA (US)

(73) Assignee: WSP Chemicals & Technology, LLC, Ambridge, PA (US)

( * ) Notice: Subject to any disclaimer, the term of this patent is extended or adjusted under 35 U.S.C. 154(b) by 536 days.

(21) Appl. No.: 10/988,366

(22) Filed: Nov. 12, 2004

(65) Prior Publication Data

US 2005/0074417 A1 Apr. 7, 2005

Related U.S. Application Data

(63) Continuation-in-part of application No. 10/228,875, filed on Aug. 27, 2002.

(60) Provisional application No. 60/339,630, filed on Dec. 12, 2001.

(51) Int. Cl.
C11D 1/02 (2006.01)
C11D 1/38 (2006.01)
C11D 1/88 (2006.01)
C11D 3/37 (2006.01)
A61K 8/00 (2006.01)

(52) U.S. Cl. .................. 510/123; 510/124; 510/127; 510/158; 510/403; 510/426; 510/433; 510/475; 510/490; 510/492; 510/499; 424/70.11; 424/70.19; 424/70.21; 424/70.22

(58) Field of Classification Search ................. 510/123, 510/124, 127, 158, 403, 426, 433, 475, 490, 510/492, 499; 424/70.11, 70.19, 70.21, 70.22
See application file for complete search history.

(56) References Cited

U.S. PATENT DOCUMENTS

| | | | |
|---|---|---|---|
| 3,018,695 A | 1/1962 | George | |
| 3,292,698 A | 12/1966 | Savins | |
| 3,361,213 A | 1/1968 | Savins | |
| 3,373,107 A | 3/1968 | Rice et al. | |
| 3,406,115 A | 10/1968 | White | |
| 3,578,871 A | 5/1971 | Sakamoto | |
| 3,604,508 A | 9/1971 | Son, Jr. | |
| 3,760,881 A | 9/1973 | Kiel | |
| 3,849,348 A | 11/1974 | Hewitt | |
| 3,892,252 A | 7/1975 | Poettmann | |
| 3,920,599 A | 11/1975 | Hurlock et al. | |
| 3,929,678 A | 12/1975 | Laughlin et al. | |
| 3,937,283 A | 2/1976 | Blauer et al. | |
| 3,954,627 A | 5/1976 | Dreher et al. | |
| 3,986,825 A | 10/1976 | Sokol | |
| 4,007,792 A | 2/1977 | Meister | |
| 4,049,608 A | 9/1977 | Steckler et al. | |
| 4,061,580 A | 12/1977 | Jahnke | |
| 4,064,091 A | 12/1977 | Samour et al. | |
| 4,071,457 A | 1/1978 | Meister | |
| 4,108,782 A | 8/1978 | Thompson | |
| 4,113,631 A | 9/1978 | Thompson | |
| 4,120,356 A | 10/1978 | Meister | |
| 4,148,736 A | 4/1979 | Meister | |
| 4,175,572 A | 11/1979 | Hsiung et al. | |
| 4,192,753 A | 3/1980 | Pye et al. | |
| 4,324,669 A | 4/1982 | Norman et al. | |
| 4,337,185 A | 6/1982 | Wessling et al. | |
| 4,360,061 A | 11/1982 | Carter et al. | |
| 4,409,110 A | 10/1983 | Borchardt et al. | |
| 4,412,586 A | 11/1983 | Sifferman | |
| 4,416,297 A | 11/1983 | Wolfram et al. | |
| 4,418,755 A | 12/1983 | Sifferman | |
| 4,432,881 A | 2/1984 | Evani | |
| 4,438,045 A | 3/1984 | Neih et al. | |
| 4,458,757 A | 7/1984 | Bock et al. | |
| 4,465,801 A | 8/1984 | Peiffer et al. | |
| 4,469,873 A | 9/1984 | Nieh | |
| 4,507,210 A | 3/1985 | Lauzon | |
| 4,517,351 A | 5/1985 | Szymanski et al. | |
| 4,534,875 A | 8/1985 | Rose | |
| 4,569,799 A | 2/1986 | House | |
| 4,579,667 A | 4/1986 | Echt et al. | |
| 4,579,670 A | 4/1986 | Payne | |
| 4,591,447 A | 5/1986 | Kubala | |

(Continued)

FOREIGN PATENT DOCUMENTS

AU 200221299 A1 5/2005

(Continued)

*Primary Examiner*—Brian P Mruk
(74) *Attorney, Agent, or Firm*—Blynn L. Shideler; Krisanne Shideler; BLK Law Group

(57) ABSTRACT

A cosmetically acceptable medium containing a component and an aqueous gel that includes water and:
 (a) a cationic polymer;
 (b) an anionic surfactant having from 8 to 22 carbon atoms, where the amount of the anionic surfactant is less than the amount of the cationic polymer;
 (c) an amphoteric surfactant, where the amount of the amphoteric surfactant is less than the amount of the cationic polymer; and
 (d) optionally a long chain amine oxide, where the amount of said long chain amine oxide is less than the amount of the cationic polymer.

The component is selected from a cationic surfactant, a conditioning agent, a synthetic amphoteric polymer, a synthetic ampholytic polymer, a synthetic non-ionic polymer, an amino acid, a protein, an oxidizing agent, a hair dye, dyes, pigments, a fragrance, one or more vitamins, and mixtures thereof. The cosmetically acceptable medium can be used to treat keratin-based substrates.

43 Claims, No Drawings

U.S. PATENT DOCUMENTS

| | | | |
|---|---|---|---|
| 4,604,217 A | 8/1986 | Lukach et al. | |
| 4,615,825 A | 10/1986 | Teot et al. | |
| 4,617,132 A | 10/1986 | Dalrymple et al. | |
| 4,637,883 A | 1/1987 | Patel et al. | |
| 4,646,834 A | 3/1987 | Bannister | |
| 4,653,584 A | 3/1987 | Bail et al. | |
| 4,662,444 A | 5/1987 | Yang | |
| 4,681,165 A | 7/1987 | Bannister | |
| 4,695,389 A | 9/1987 | Kubala | |
| 4,702,848 A | 10/1987 | Payne | |
| 4,707,306 A | 11/1987 | Leighton et al. | |
| 4,710,586 A | 12/1987 | Patel et al. | |
| 4,725,372 A | 2/1988 | Teot et al. | |
| 4,735,731 A | 4/1988 | Rose et al. | |
| 4,737,296 A | 4/1988 | Watkins | |
| 4,743,384 A | 5/1988 | Lu et al. | |
| 4,770,814 A | 9/1988 | Rose et al. | |
| 4,778,865 A | 10/1988 | Leighton et al. | |
| 4,779,680 A | 10/1988 | Sydnask | |
| 4,790,958 A | 12/1988 | Teot | |
| 4,796,702 A | 1/1989 | Scherubel | |
| 4,803,071 A | 2/1989 | Iovone et al. | |
| 4,806,256 A | 2/1989 | Rose et al. | |
| 4,831,092 A | 5/1989 | Bock et al. | |
| 4,834,182 A | 5/1989 | Shu | |
| 4,852,652 A | 8/1989 | Kuehne | |
| 4,880,565 A | 11/1989 | Rose et al. | |
| 4,910,248 A | 3/1990 | Peiffer | |
| 4,911,241 A | 3/1990 | Williamson et al. | |
| 4,923,694 A | 5/1990 | Shih et al. | |
| 4,948,576 A | 8/1990 | Verdicchio et al. | |
| 4,975,482 A | 12/1990 | Peiffer | |
| 4,988,450 A | 1/1991 | Wingrave et al. | |
| 5,036,136 A | 7/1991 | Peiffer | |
| 5,049,383 A | 9/1991 | Huth et al. | |
| 5,062,969 A | 11/1991 | Holtmyer et al. | |
| 5,089,252 A | 2/1992 | Grollier et al. | |
| 5,093,448 A | 3/1992 | Peiffer | |
| 5,101,903 A | 4/1992 | Liave et al. | |
| 5,105,884 A | 4/1992 | Sydansk | |
| 5,125,456 A | 6/1992 | Hutchins et al. | |
| 5,129,457 A | 7/1992 | Sydansk | |
| 5,137,715 A | 8/1992 | Hoshowski et al. | |
| 5,159,979 A | 11/1992 | Jennings, Jr. | |
| 5,162,475 A | 11/1992 | Tang et al. | |
| 5,169,441 A | 12/1992 | Lauzon | |
| 5,203,411 A | 4/1993 | Dawe et al. | |
| 5,246,072 A | 9/1993 | Frazier, Jr. et al. | |
| 5,258,137 A | 11/1993 | Bonekamp et al. | |
| 5,276,248 A | 1/1994 | Engelhardt et al. | |
| 5,310,002 A | 5/1994 | Blauch et al. | |
| 5,362,827 A | 11/1994 | Bock | |
| 5,462,689 A | 10/1995 | Choy et al. | |
| 5,529,122 A | 6/1996 | Thatch | |
| 5,547,026 A | 8/1996 | Brannon et al. | |
| 5,551,516 A | 9/1996 | Norman et al. | |
| 5,562,866 A | 10/1996 | Hu et al. | |
| 5,566,760 A | 10/1996 | Harris | |
| 5,573,709 A | 11/1996 | Wells | |
| 5,587,356 A | 12/1996 | Dauderman et al. | |
| 5,591,701 A | 1/1997 | Thomas | |
| 5,597,783 A | 1/1997 | Audibert et al. | |
| 5,607,904 A | 3/1997 | Jarrett | |
| 5,637,556 A | 6/1997 | Argillier et al. | |
| 5,652,200 A | 7/1997 | Davies et al. | |
| 5,670,460 A | 9/1997 | Neely et al. | |
| 5,679,877 A | 10/1997 | Erlli et al. | |
| 5,701,955 A | 12/1997 | Frampton | |
| 5,705,467 A | 1/1998 | Choy | |
| 5,706,895 A | 1/1998 | Sydansk | |
| 5,707,955 A | 1/1998 | Gomes et al. | |
| 5,711,376 A | 1/1998 | Sydansik | |
| 5,728,654 A | 3/1998 | Dobson, Jr. et al. | |
| 5,735,349 A | 4/1998 | Dawson et al. | |
| 5,741,757 A | 4/1998 | Cooper et al. | |
| 5,767,050 A | 6/1998 | Adamy et al. | |
| 5,785,747 A | 7/1998 | Volimer et al. | |
| 5,846,308 A | 12/1998 | Lauzon | |
| 5,869,442 A | 2/1999 | Srinivas et al. | |
| 5,964,295 A | 10/1999 | Brown et al. | |
| 5,965,502 A | 10/1999 | Balzer | |
| 5,979,555 A | 11/1999 | Gadberry et al. | |
| 6,011,075 A | 1/2000 | Parris et al. | |
| 6,020,289 A | 2/2000 | Dymond | |
| 6,035,936 A | 3/2000 | Whalen | |
| 6,063,737 A | 5/2000 | Haberman et al. | |
| 6,068,056 A | 5/2000 | Frenier et al. | |
| 6,069,118 A | 5/2000 | Hinkel et al. | |
| 6,076,046 A | 6/2000 | Vasudevan et al. | |
| 6,100,222 A | 8/2000 | Volimer et al. | |
| 6,103,153 A | 8/2000 | Park et al. | |
| 6,106,700 A | 8/2000 | Collins et al. | |
| 6,110,451 A | 8/2000 | Matz et al. | |
| 6,140,277 A | 10/2000 | Tibbles et al. | |
| 6,143,709 A | 11/2000 | Carey | |
| 6,156,805 A | 12/2000 | Smith et al. | |
| 6,169,058 B1 | 1/2001 | Lee et al. | |
| 6,172,010 B1 | 1/2001 | Argillier et al. | |
| 6,192,985 B1 | 2/2001 | Hinkel et al. | |
| 6,194,354 B1 | 2/2001 | Hatchman | |
| 6,194,356 B1 | 2/2001 | Jones et al. | |
| 6,221,817 B1 | 4/2001 | Guskey et al. | |
| 6,227,295 B1 | 5/2001 | Mitchell et al. | |
| 6,230,805 B1 | 5/2001 | Vercaemer et al. | |
| 6,232,274 B1 | 5/2001 | Hughes et al. | |
| 6,239,183 B1 | 5/2001 | Farmer et al. | |
| 6,248,317 B1 | 6/2001 | Snyder et al. | |
| 6,258,859 B1 | 7/2001 | Dahayanake et al. | |
| 6,268,314 B1 | 7/2001 | Hughes et al. | |
| 6,279,656 B1 | 8/2001 | Sinclair et al. | |
| 6,281,180 B1 | 8/2001 | Tartakovsky et al. | |
| 6,283,212 B1 | 9/2001 | Hinkel et al. | |
| 6,284,230 B1 | 9/2001 | Sako et al. | |
| 6,297,203 B1 | 10/2001 | Gusky et al. | |
| 6,302,209 B1 | 10/2001 | Thompson et al. | |
| 6,305,470 B1 | 10/2001 | Woie | |
| 6,306,800 B1 | 10/2001 | Samuel et al. | |
| 6,315,824 B1 | 11/2001 | Lauzon | |
| 6,350,721 B1 | 2/2002 | Fu et al. | |
| 6,359,040 B1 | 3/2002 | Burdick | |
| 6,399,546 B1 | 6/2002 | Chang et al. | |
| 6,399,547 B1 | 6/2002 | Frenier et al. | |
| 6,403,537 B1 | 6/2002 | Chesser et al. | |
| 6,410,489 B1 | 6/2002 | Zhang et al. | |
| 6,417,268 B1 | 7/2002 | Zhang et al. | |
| 6,432,885 B1 | 8/2002 | Volimer | |
| 6,433,075 B1 | 8/2002 | Davies et al. | |
| 6,446,727 B1 | 9/2002 | Zemlak et al. | |
| 6,468,945 B1 | 10/2002 | Zhang | |
| 6,474,413 B1 | 11/2002 | Barbosa et al. | |
| 6,482,866 B1 | 11/2002 | Dahayanake et al. | |
| 6,488,091 B1 | 12/2002 | Weaver et al. | |
| 6,489,270 B1 | 12/2002 | Volimer et al. | |
| 6,491,099 B1 | 12/2002 | Di Lullo Arias et al. | |
| 6,506,710 B1 | 1/2003 | Hoey et al. | |
| 6,508,307 B1 | 1/2003 | Almaguer | |
| 6,509,300 B1 | 1/2003 | Gupta | |
| 6,509,301 B1 | 1/2003 | Volimer | |
| 6,534,449 B1 | 3/2003 | Gilmour et al. | |
| 6,569,814 B1 | 5/2003 | Brady et al. | |
| 6,573,305 B1 | 6/2003 | Thunhorst et al. | |
| 6,575,242 B2 | 6/2003 | Woie | |
| 6,579,947 B2 | 6/2003 | Heitz et al. | |
| 6,586,371 B1 | 7/2003 | Maroy et al. | |

| | | |
|---|---|---|
| 6,605,570 B2 | 8/2003 | Miller et al. |
| 6,719,053 B2 | 4/2004 | Thompson |
| 6,720,090 B2 | 4/2004 | England et al. |
| 6,762,154 B2 | 7/2004 | Lungwitz et al. |
| 6,793,018 B2 | 9/2004 | Dawson et al. |
| 6,884,760 B1 | 4/2005 | Brand et al. |
| 7,205,262 B2 * | 4/2007 | Schwartz et al. ............... 507/90 |
| 2002/0002205 A1 | 1/2002 | Dahayanake et al. |
| 2002/0004464 A1 | 1/2002 | Nelson et al. |
| 2002/0033260 A1 | 3/2002 | Lungwitz et al. |
| 2002/0125012 A1 | 9/2002 | Dawson et al. |
| 2002/0132741 A1 | 9/2002 | Chang et al. |
| 2002/0147114 A1 | 10/2002 | Dobson et al. |
| 2002/0185278 A1 | 12/2002 | Brown et al. |
| 2002/0189810 A1 | 12/2002 | DiLuillo et al. |
| 2002/0193257 A1 | 12/2002 | Lee et al. |
| 2003/0008781 A1 | 1/2003 | Gupta et al. |
| 2003/0008803 A1 | 1/2003 | Nilsson et al. |
| 2003/0019627 A1 | 1/2003 | Qu et al. |
| 2003/0040441 A1 | 2/2003 | Miller et al. |
| 2003/0040546 A1 | 2/2003 | Dahayanake et al. |
| 2003/0073585 A1 | 4/2003 | Di Luilo Arias et al. |
| 2003/0119680 A1 | 6/2003 | Chang et al. |
| 2003/0130133 A1 | 7/2003 | Volimer |
| 2003/0134751 A1 | 7/2003 | Lee et al. |
| 2003/0139298 A1 | 7/2003 | Fu et al. |
| 2003/0168217 A1 | 9/2003 | Zhang et al. |
| 2004/0011527 A1 | 1/2004 | Jones et al. |
| 2004/0035579 A1 | 2/2004 | Parlar et al. |
| 2004/0053789 A1 | 3/2004 | Jones et al. |
| 2004/0067855 A1 | 4/2004 | Hughes et al. |

FOREIGN PATENT DOCUMENTS

| | | |
|---|---|---|
| CA | 1 185 779 | 4/1985 |
| CA | CA 2 329 600 | 6/2002 |
| EP | 0 280 341 | 8/1988 |
| EP | 0 308 189 | 3/1989 |
| EP | 0 308 190 | 3/1989 |
| EP | WO 00/06102 * | 2/2000 |
| EP | 1 042 425 B1 | 11/2002 |
| EP | 1 273 756 A1 | 1/2003 |
| EP | 1 051 452 B1 | 3/2003 |
| EP | 1 323 888 A1 | 7/2003 |
| WO | WO 99/50530 | 10/1999 |
| WO | WO 00/39241 | 7/2000 |
| WO | WO 01/23703 A1 | 4/2001 |
| WO | WO 01/51767 A2 | 7/2001 |
| WO | WO 01/94742 A1 | 12/2001 |
| WO | WO 02/24771 A2 | 3/2002 |
| WO | WO 02/064946 A1 | 8/2002 |
| WO | WO 02/064947 A1 | 8/2002 |
| WO | WO 02/066790 A1 | 8/2002 |
| WO | WO 02/070862 A1 | 9/2002 |
| WO | WO 02/088520 A1 | 11/2002 |
| WO | WO 03/015523 A2 | 2/2003 |
| WO | WO 03/018695 A1 | 3/2003 |
| WO | WO 03/048267 A1 | 5/2003 |
| WO | WO 03/054352 A1 | 7/2003 |
| WO | WO 03/056130 A1 | 7/2003 |

* cited by examiner

POLYMERIC GEL SYSTEM AND COMPOSITIONS FOR TREATING KERATIN SUBSTRATES CONTAINING SAME

REFERENCES TO RELATED APPLICATIONS

This application is a Continuation In Part (CIP) of application Ser. No. 10/228,875, filed Aug. 27, 2002 pending, which claims priority to Provisional Application No. 60/339,630, filed Dec. 12, 2001.

BACKGROUND OF THE INVENTION

1. Field of the Invention

The present invention relates to novel keratin-treating compositions containing polymer-surfactant compositions and methods for using such compositions in personal care applications. The compositions are useful in treating keratin-containing substrates. Keratin substrates include, but are not limited to, animal and human skin, hair and nails. More specifically, the present invention relates to cosmetically acceptable compositions containing the compositions and methods for treating keratin.

2. Brief Description of Prior Art

There has been a long-standing desire to discover new ingredients and formulations that will improve the topical and bulk condition of keratin-based substrates such as hair, skin and nails. For example, such ingredients must have adequate adherent properties, so that they are not only adsorbed initially, but are also retained on exposure to water. This property is referred to as "substantivity," i.e., the ability of a material to be adsorbed onto keratin and to resist removal by water rinse-off.

Hair is composed of keratin, a sulfur-containing fibrous protein. The isoelectric point of keratin, and more specifically of hair, is generally in the pH range of 3.2-4.0. Therefore, at the pH of a typical shampoo, hair carries a net negative charge. Consequently, cationic polymers have long been used as conditioners in shampoo formulations or as a separate treatment in order to improve the combability of both dry and wet hair. The substantivity of the cationic polymers for negatively charged hair coupled with film formation facilitates detangling during wet hair combing and a reduction in static flyaway during the combing of dry hair. Cationic polymers generally also impart softness and suppleness to hair.

When cationic polymers are added to shampoos (or to skin care products such as cleaning compositions) containing anionic surfactants, the formation of highly surface active association complexes generally takes place, which imparts improved foam stability to the shampoo. Maximum surface activity and foam stability, or lather, are achieved at near stoichiometric ratios of anionic surfactant to cationic polymer, where the complex is at least water soluble. Generally, cationic conditioners exhibit some incompatibility at these ratios. Compatibility gives a clear formulation, which is more desirable commercially. Incompatibility leads to a haze or precipitation, which may be aesthetically less desirable in some formulations.

Hair fixative properties, such as curl retention, are believed to be directly related to film-forming properties of cationic polymers, as well as to molecular weight, with performance generally increasing with increasing molecular weight. However, the fixative properties conferred by cationic polymers generally tend to have a reciprocal relationship to other conditioning properties, i.e., good curl retention usually means that properties such as wet combability will suffer and vice versa.

Keratin conditioning additives generally are of three primary types: cationic polymers, proteins or protein derivatives, and fatty quaternary ammonium compounds. Commonly used cationic polymers include: quaternary nitrogen-containing hydroxyethyl cellulose compounds, copolymers of vinylpyrrolidone and dimethylamino-ethylmethacrylate and mino functional polydimethyl-siloxane. Hydrolyzed animal protein has been frequently used as a keratin conditioner. Also used are natural products such as collagen and casein. Suitable quaternary ammonium compounds include such products as stearyl dimethyl ammonium chloride.

Generally, two broad areas of skin care products have been recognized as skin conditioners: emollients and humectants. Emollients generally provide improved moisture retention in the skin and plasticization or softening of the skin. Common commercial emollients include mineral oil, petrolatum, aliphatic alcohols such as stearyl alcohol, lanolin and its derivatives, glycol stearate, and fatty acids such as triethanolamine oleate. Humectants generally attract moisture, retard evaporation of water from the skin or hair surface and plasticize/soften skin. Common commercial humectants include glycerin, propylene glycol, sorbitols and polyethylene glycols.

A desirable skin conditioner should impart at least some of the attributes of an emollient or a humectant, as well as provide improved lubricity and feel to the skin after treatment and/or reduce the skin irritation caused by other components in the conditioner such as, for example, soaps, detergents, foam boosters, surfactants and perfumes. It is known by those skilled in the art that cationic polymers may be employed as skin and nail conditioners.

Sometimes, it is also desirable that the ingredients of skin and nail care products have adequate adherent properties, so that they are not only adsorbed initially, but are also retained upon exposure to water. In hair care applications, this property is referred to as "substantivity," i.e., the ability of a material contacted with keratin of skin or nails to resist removal by water rinse-off. Generally, in the pH that is typical of use conditions, the skin and nails carry a net negative charge. Consequently, cationic polymers have long since been used as conditioners in nail and skin care formulations. The substantivity of the cationic polymers for negatively charged skin and nails leads to film formation that facilitates lubricity, moisturizing and feel.

The skin and nail conditioning properties of lubricity, moisturizing and feel are related to the film-forming properties of the cationic polymers, as well as to molecular weight, with performance increasing with increasing molecular weight, generally.

Conditioning additives including copolymers of dimethyldiallylammonium chloride and other monomers are well known; see, e.g., EP 0308189 (with acrylamide) and EP 0308190 and U.S. Pat. No. 4,803,071 (with hydroxyethyl cellulose). Amphoteric betaines have also been employed in cosmetic compositions; see GB 2,113,245 which discloses use of betainized dialkylaminoalkyl(meth)acrylate together with a cationic polymer.

The use of polymers of dimethyldiallylammonium chloride (DMDAAC) in the treatment of keratin is also known and disclosed in, for example, U.S. Pat. Nos. 4,175,572 and 3,986,825.

U.S. Pat. No. 4,923,694 to Shih et al. discloses copolymers of vinyl pyrrolidone and (meth)acrylic cationic monomers that are useful for treating hair. These polymers are able to provide good hair styling properties at low concentrations of cationic monomer, but provide limited substantivity due to their low cationic charge density. When the cationic charge density is increased, the polymers disclosed by Shih et al.

become difficult to formulate with because of their decreasing compatibility with anionic surfactants.

As disclosed in U.S. Pat. No. 4,940,576 to Walsh, an excess of anionic surfactant is required when formulating with cationic polymers. The amount of the surfactant is in the range of 0.9 to 2.0 moles times the amount of the surfactant necessary to result in complete neutralization of the charges on the polymer.

There remains a need for a polymeric conditioning additive for keratin-based substrates that is easy to formulate with (easy to make clear surfactant-based formulations), provides excellent hair styling properties as well as excellent conditioning properties to hair, skin and nails.

SUMMARY OF THE INVENTION

The present invention is directed to a cosmetically acceptable medium that contains a component and an aqueous gel that includes water and, by weight based on the water,
(a) from 0.1% to 5% of a cationic polymer;
(b) from 0.05% to 0.5% of an anionic surfactant having from 8 to 22 carbon atoms, where the amount of the anionic surfactant is less than the amount of the cationic polymer;
(c) from 0.001% to 0.5% of an amphoteric surfactant, where the amount of the amphoteric surfactant is less than the amount of the cationic polymer; and
(d) up to 0.5% of a long chain amine oxide, where the amount of said long chain amine oxide is less than the amount of the cationic polymer.

The component is selected from a cationic surfactant, a conditioning agent, a synthetic amphoteric polymer, a synthetic ampholytic polymer, a synthetic non-ionic polymer, an amino acid, a protein, an oxidizing agent, a hair dye, dyes, pigments, a fragrance, one or more vitamins, and mixtures thereof.

The present invention also provides a method for treating keratin-based substrates that includes contacting the keratin-based substrate with the above-described composition.

DESCRIPTION OF THE PREFERRED EMBODIMENTS

Other than in the operating examples or where otherwise indicated, all numbers or expressions referring to quantities of ingredients, reaction conditions, etc. used in the specification and claims are to be understood as modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

As used herein, the term "substantially free" is meant to indicate that a material can be present in an incidental amount or that a particular occurrence or reaction only takes place to an insignificant extent, which does not affect desired properties. In other words, the material is not intentionally added to an indicated composition, but may be present at minor or inconsequential levels, for example, because it was carried over as an impurity as part of an intended composition component.

As used herein, the terms "(meth)acrylic" and "(meth)acrylate" are meant to include both acrylic and methacrylic acid derivatives, such as the corresponding alkyl esters often referred to as acrylates and (meth)acrylates, which the term (meth)acrylate is meant to encompass.

As used herein, the term "polymer" is meant to encompass oligomer, and includes without limitation both homopolymers and copolymers.

As used herein, the phrase components "are different from each other" refers to components that do not have the same chemical structure as other components in the composition.

As used herein, the term "water-soluble," when used in relation to polymers, refers to polymers that form a solution in water that is free of insoluble polymer particles. The determination that a solution is free of insoluble polymer particles can be made using conventional light scattering techniques or by passing the solution through a sufficiently fine filter screen capable of capturing insoluble polymer particles.

As used herein, the terms "branching" and "branched polymers" refer to the arms of polymers that have a main backbone with arms extending therefrom, are not interconnected with other polymer molecules and are water-soluble. Polymers that contain branching are distinguished from crosslinked polymers in that crosslinked polymers are polymers that are branched and interconnected with other polymer molecules to the point that they form a three-dimensional network and are not water-soluble, while branched polymers retain their water solubility.

As used herein, the term "keratin" refers to human or animal hair, skin and/or nails.

As used herein, the term "effective amount" refers to that amount of a composition necessary to bring about a desired result, such as, for example, the amount needed to treat a keratin-containing substrate relative to a particular purpose, such as conditioning.

As used herein the term "cosmetically acceptable medium" refers to formulations that are used to treat skin, hair and/or nails and contain one or more ingredients used by those skilled in the art to formulate products used to treat skin, hair and/or nails. The cosmetically acceptable medium may be in any suitable form, i.e., a liquid, cream, emulsion, gel, thickening lotion or powder and will typically contain water, and may contain a cosmetically acceptable solvent and/or one or more surfactants.

Unless otherwise specified, the term "molecular weight" refers to the weight average molecular weight of a polymer as determined using gel permeation chromatography with polystyrene or sulfonated polystyrene standards.

Unless otherwise indicated, the term "viscosity" indicates the viscosity of a liquid in cps measured using a BROOK- FIELD® Viscometer (Brookfield Engineering, Stoughton, Mass.) Model RV using an appropriate spindle at 10 rpm and 25° C.

The present invention provides a cosmetically acceptable medium including a component and an aqueous gel. The component is selected from a cationic surfactant, a conditioning agent, a water insoluble liquid, a synthetic amphoteric polymer, a synthetic ampholytic polymer, a synthetic nonionic polymer, an amino acid, a protein, an oxidizing agent, a hair dye, dyes, pigments, a fragrance, one or more vitamins, and mixtures thereof.

In an embodiment of the invention, the cosmetically acceptable medium has a viscosity of at least 500 cps, in some cases at least 1,000 cps and in other cases at least 1,500 cps. Desirably, the use of low molecular weight alcohols, such as ethanol, and low molecular weight glycols, such as ethylene glycol and glycerol, are avoided as they tend to impair the viscosity of the cosmetically acceptable medium.

As used herein, the term "vitamins" refers to any of the group of organic compounds which are essential for normal nutrition and have to be supplied to the body because they cannot be synthesized by the body. Non-limiting examples of vitamins that can be used in the present invention include retinol (vitamin A) and its derivatives such as retinyl pahnitate; tocopherol (vitamin E); vitamin D (ergocalciferol) and its derivatives; vitamin E (alpha-tocopherol), its derivatives or its esters such as tocopheryl acetate; vitamin B6 or pyridoxine; ascorbic acid (vitamin C), as well as mixtures of vitamins C, CP and CG; vitamin mixtures such as Septival EPC (phosphoric diester of vitamin E and C) from Seppic; vitamin D2 (calciferol); vitamin D3 (cholecalciferol); vitamin B1 (thiamin); vitamin B2 (riboflavin); vitamin B3 (niacin); vitamin B4; vitamin B6 (pyridoxine); vitamin B12; vitamin K and mixtures with provitamins such as beta-carotene, biotin, and panthenol and its derivatives; derivatives thereof and combinations thereof. In an embodiment of the invention, water-soluble or water-dispersible derivatives of vitamins are used. When included, vitamins can be included in the present cosmetically acceptable medium at a level of from 0.001 to 1 wt. %, in some cases 0.005 to 0.5 wt. % and in other cases from 0.01 to 0.25 wt. % based on the weight of the cosmetically acceptable medium.

The proteins that can optionally be included in the present cosmetically acceptable medium include, but are not limited to, hydrolyzed milk protein, hydrolyzed silk protein, hydrolyzed soy protein, hydrolyzed wheat protein, hydrolyzed collagen, hydrolyzed keratin and those available under the trade names MACKPRO® KLP, MACKPRO® WLW, MACKPRO® MLP, MACKPRO® NSP, MACKPRO® NLW, MACKPRO® WWP, MACKPRO® NLP and MACKPRO® SLP, available from McIntyre Group, Ltd., University Park, Ill. When included, proteins can be included in the present cosmetically acceptable medium at a level of from 0.01 to 5 wt. %, in some cases 0.1 to 2.5 wt. % and in other cases from 0.25 to 1 wt. % based on the weight of the cosmetically acceptable medium.

The oxidizing agents that can optionally be included in the present cosmetically acceptable medium include, but are not limited to, peroxides such as diacyl peroxides, non-limiting examples being dibenzoyl peroxide, succinic acid peroxide, dilauroyl peroxide and didecanoyl peroxide; dialkyl peroxides, non-limiting examples being dicumyl peroxide, $\alpha,\alpha'$-di(t-butylperoxy)diisopropylbenzenes, 2,5-dimethyl-2,3-di-(t-butylperoxy)hexane, di-t-butyl peroxide, hydrogen peroxide, methyl ethyl ketone peroxides, benzoyl peroxides, di-t-butyl peroxide, 2,5-dimethyl-2,3-di-(t-butylperoxy)hexyne-3; tertiary alkyl hydroperoxides, non-limiting examples being 2,5-dihydroperoxy-2,5-dimethyl hexane, cumene hydroperoxide, t-butyl hydroperoxide, t-amyl hydroperoxide; hydrogen peroxide; peroxydicarbonates; peroxyesters; peroxyketals; and combinations thereof. Suitable oxidizing agents include those available under the trade name LUPEROX® from Atofina Chemicals, Inc., Philadelphia, Pa. In an embodiment of the invention, the oxidizing agent is selected from hydrogen peroxide and benzoyl peroxide. When included, the oxidizing agents can be included in the present cosmetically acceptable medium at a level of from 0.01 to 5 wt. %, in some cases 0.1 to 2.5 wt. % and in other cases from 0.25 to 1 wt. % based on the weight of a liquid cosmetically acceptable medium. In some embodiments, the cosmetically acceptable medium is in a dry form, which can be reconstituted in water. In such a situation, oxidizing agents that are solid at ambient conditions are used and can make up from 0.1 to 50 wt. %, in some cases 0.5 to 25 wt. % and in other cases 1 to 10 wt. % of the cosmetically acceptable medium in dry form.

The aqueous gel comprises water and a cationic polymer, an anionic surfactant having from about 8 to about 22 carbon atoms, optionally a hydrophobic alcohol, an amphoteric surfactant, and optionally a long chain an amine oxide, i.e., an amine oxide of a $C_8$-$C_{32}$ linear, branched or cyclic aliphatic amine.

In an embodiment of the invention, the gel has a Zeta Potential of an absolute value of at least 20 millivolts.

The cosmetically acceptable medium can be a skin or hair care gel product, such as a hair dye, a styling product or rinse, or a skin care. Non-limiting examples include an aftershave, a sunscreen, a hand lotion, a shaving cream, a permanent wave, a hair relaxer, a hair bleach, a hair setting composition, a styling gel and a powder that can be reconstituted into a gel when mixed with water.

The present composition can be in liquid form or can be dried to be in a dry, or in some cases powder, form. Dry ingredients can be added by dry blending them with the powder prior to the gel being reconstituted. The dry form of the composition of the present invention can be reconstituted in an appropriate solvent, typically an aqueous solvent, in order to reform a gel in accordance with the invention.

In an embodiment of the invention, the cosmetically acceptable medium according to the invention is in dry or powder form and is capable of being reconstituted into a gel by mixing into water.

As used herein, the term "cationic polymers" refers to polymers that contain at least 50, in some cases at least 60 and in other cases at least 75 mole % repeat units resulting from the polymerization of one or more ethylenically unsaturated monomers that contain a cationic group, desirably a quaternary ammonium group. The present cationic polymers can optionally contain up to 20, in some cases up to 10 and in other cases up to 5 mole % of repeat units resulting from the polymerization of one or more ethylenically unsaturated monomers that contain an acid functional group, desirably a carboxylic acid or a sulfonic acid functional group. The cationic polymers can also optionally include repeat units resulting from the polymerization of one or more nonionic ethylenically unsaturated monomers.

In one embodiment of the invention, at least 20% of the repeat units of the cationic polymer that are added to the aqueous gel are derived from dimethyl diallyl ammonium chloride.

In a further embodiment, the cationic polymer may include residues from one or more monomers selected from diallyl dialkyl ammonium halides, vinyl amine, (meth)acrylamide, vinyl pyrrolidone, (meth)acrylamidopropyltrimethyl ammonium halides, (meth)acryloyloxyethyltrimethyl ammonium halides and (meth)acryloyloxyethyltrimethyl ammonium methyl sulfate.

In an even further embodiment, the molecular weight of the cationic polymer is at least 10,000.

The amount of cationic polymer present in the aqueous gel is at least 0.05 wt. %, in some cases at least 0.1 wt. %, in other cases at least 0.2 wt. %, in some instances at least 0.25 wt. % and in some situations at least 0.5 wt. % of the aqueous gel. Additionally, the amount present in the aqueous gel is up to 5 wt. %, in some cases up to 3 wt. %, in other cases up to 2 wt. % and in some instances up to 1.5 wt. %. The amount of cationic polymer can be any value or range between any of the values recited above. All weight percents are based on the water.

The amount of anionic surfactant present in the aqueous gel is at least 0.001 wt. %, in some cases at least 0.01 wt. %, in other cases at least 0.05 wt. % and in some situations at least 0.1 wt. % of the cosmetically acceptable medium. Additionally, the amount present in the aqueous gel is up to 0.5 wt. %, in some cases up to 0.35 wt. %, in other cases up to 0.25 wt. % and in some instances up to 0.25 wt. %. The amount of anionic surfactant used is an amount sufficient to cause the aqueous gel to have its desired viscosity. The amount of anionic surfactant can be any value or range between any of the values recited above and will be present at a level that is less than that of the cationic polymer. All weight percents are based on the water.

Anionic surfactants useful herein include those that are disclosed in U.S. Pat. No. 5,573,709 to Wells, the disclosure of which is herein incorporated by reference in its entirety. Examples include, but are not limited to, alkyl and alkyl ether sulfates. Specific non-limiting examples include alkyl ether sulfates such as sodium and ammonium salts of lauryl sulfate, lauryl ether sulfate, coconut alkyl triethylene glycol ether sulfate, tallow alkyl triethylene glycol ether sulfate and tallow alkyl hexaoxyethylene sulfate. More particular non-limiting examples of alkyl ether sulfates are those including a mixture of individual compounds, said mixture having an average alkyl chain length of from about 12 to about 16 carbon atoms and an average degree of ethoxylation of from about 1 to about 6 moles of ethylene oxide.

Another suitable class of anionic surfactants are the alkyl sulfuric acid salts. Non-limiting examples are the salts of an organic sulfuric acid reaction product of a hydrocarbon of the methane series, including iso-, neo-, ineso- and n-paraffins, having about 8 to about 24 carbon atoms, typically, about 12 to about 18 carbon atoms and a sulfonating agent, e.g., $SO_3$, $H_2SO_4$, obtained according to known sulfonation methods, including bleaching and hydrolysis. Particular non-limiting examples include alkali metal and ammonium sulfated $C_{12}$-$C_{38}$ n-paraffins.

Additional non-limiting examples of synthetic anionic surfactants which come within the terms of the present invention are the olefin sulfonates, the beta-alkyloxy alkalene sulfonates, and the reaction products of fatty acids esterified with isethionic acid and neutralized with sodium hydroxide, as well as succinamates. Specific non-limiting examples of succinamates include disodium N-octadecyl sulfosuccinamate, tetrasodium N-(1,2-dicarboxyethyl)-N-octadecylsulfosuccinamate, diamyl ester of sodium sulfosuccinic acid, dihexyl ester of sodium sulfosuccinic acid and dioctyl esters of sodium sulfosuccinic acid.

Many additional synthetic anionic surfactants are described in U.S. Pat. No. 3,929,678 to Laughlin et al., which is herein incorporated by reference in its entirety.

In an embodiment of the invention, the anionic surfactants used in the present compositions may include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfonate, triethanolamine 1-lauryl sulfate, triethanolamine lauryl sulfonate, monoethanolamine cocoyl sulfate, monoethanolamine lauryl sulfonate, sodium tridecyl benzene sulfonate, sodium dodecyl benzene sulfonate, disodium N-octadecyl sulfosuccinamate, tetrasodium N-(1,2-dicarboxyethyl)-N-octadecylsulfosuccinamate, diamyl ester of sodium sulfosuccinic acid, dihexyl ester of sodium sulfosuccinic acid and dioctyl esters of sodium sulfosuccinic acid.

In an embodiment of the invention, the cosmetically acceptable medium of the present invention contains the cationic polymer and anionic surfactant at levels such that the equivalent ratio of cationic groups in the cationic polymer to the moles of amphoteric surfactant is at least 2, in some cases at least 3 and in other cases at least 5. Also, the equivalent ratio of cationic groups in the cationic polymer to the moles of anionic surfactant can be up to 20, in some cases up to 15, in other cases up to 10, in some instances up to 7.5 and in other instances up to 5. The equivalent ratio is a value where the aqueous gel will have its desired viscosity. The equivalent ratio of cationic groups in the cationic polymer to the moles of anionic surfactant can be any value or range between any of the values recited above.

In one embodiment, the optional hydrophobic alcohol can be a linear or branched alkyl alcohol of the general formula $C_MH_{2M+2-N}(OH)_N$, where M is a number from 6-23, and N is 1 when M is 6-12, but where M is 13-23, N may be a number from 1 to 3. In a further embodiment, the alkyl alcohol is a linear monohydric alcohol having from about 8-15 carbon atoms. In an even further embodiment, the alkyl alcohol comprises lauryl alcohol.

The amount of hydrophobic alcohol present in the aqueous gel is at least 0.001 wt. %, in some cases at least 0.05 wt. %, in other cases at least 0.01 wt. %, in some instances at least 0.1 wt. % and in some situations at least 0.25 wt. % of the cosmetically acceptable medium. Additionally, the amount present in the aqueous gel is up to 3 wt. %, in some cases up to 2.5 wt. %, in other cases up to 2 wt. % and in some situations up to 1 wt. %. All weight percents are based on the water. The amount of hydrophobic alcohol can be or can range between any of the values recited above.

The keratin cleansing compositions of the present invention contain an amphoteric surfactant. In an embodiment of the invention, the amphoteric surfactant comprises a betaine or sultaine surfactant.

Any suitable amphoteric surfactant can be used in the present invention. Suitable amphoteric surfactants are those that allow the aqueous gel to have its desired visclosity and include, but are not limited to, 3-dodecyl-aminopropionate, sodium 3-dodecylaminopropane sulfonate, sodium lauryl sarcosinate, N-alkyltaurines, coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine, amidobetaines and amidosulfobetaines.

In a particular embodiment of the invention, the amphoteric surfactant is cocamidopropyl betaine.

The amount of amphoteric surfactant present in the aqueous gel is at least 0.001 wt. %, in some cases at least 0.01 wt. %, in other cases at least 0.05 wt. % and in some situations at least 0.1 wt. % of the cosmetically acceptable medium. Additionally, the amount present in the aqueous gel is up to 0.5 wt. %, in some cases up to 0.35 wt. %, in other cases up to 0.25 wt. % and in some instances up to 0.25 wt. %. The amount of amphoteric surfactant used is an amount sufficient to cause the aqueous gel to have its desired viscosity. The amount of amphoteric surfactant can be any value or range between any of the values recited above and will be present at a level that is less than that of the cationic polymer. All weight percents are based on the water.

In an embodiment of the invention, the cosmetically acceptable medium of the present invention contains the cationic polymer and amphoteric surfactant at levels such that the equivalent ratio of cationic groups in the cationic polymer to the moles of amphoteric surfactant is at least 2, in some cases at least 3 and in other cases at least 5. Also, the equivalent ratio of cationic groups in the cationic polymer to the moles of amphoteric surfactant can be up to 50, in some cases up to 45, in other cases up to 40, in some instances up to 35 and in other instances up to 25. The equivalent ratio is a value where the aqueous gel will have its desired viscosity. The equivalent ratio of cationic groups in the cationic polymer to the moles of amphoteric surfactant can be any value or range between any of the values recited above.

The gel can optionally further include at least one amine oxide. Suitable amine oxides include cocoamidopropyl dimethyl amine oxide and other compounds of the formula $R^1R^2R^3N\rightarrow O$ wherein $R^3$ is a hydrocarbyl or substituted hydrocarbyl having from about 8 to about 30 carbon atoms, and $R^1$ and $R^2$ are independently hydrogen, a hydrocarbyl or substituted hydrocarbyl having up to 30 carbon atoms. In one embodiment, $R^3$ is an aliphatic or substituted aliphatic hydrocarbyl having at least about 12 and up to about 24 carbon atoms. In another embodiment $R^3$ is an aliphatic group having at least about 12 carbon atoms and having up to about 22 and in another embodiment an aliphatic group having at least about 18 and no more than about 22 carbon atoms. In an embodiment of the invention, the amine oxide is lauryl amine oxide.

When present, the amount of amine oxide present in the aqueous gel is at least 0.001 wt. %, in some cases at least 0.01 wt. %, in other cases at least 0.05 wt. % and in some situations at least 0.1 wt. % of the cosmetically acceptable medium. Additionally, the amount present in the aqueous gel is up to 0.5 wt. %, in some cases up to 0.35 wt. %, in other cases up to 0.25 wt. % and in some instances up to 0.25 wt. %. The amount of amine oxide used is an amount sufficient to cause the aqueous gel to have its desired viscosity. The amount of amine oxide can be any value or range between any of the values recited above and will be present at a level that is less than that of the cationic polymer. All weight percents are based on the water.

In an embodiment of the invention, the cosmetically acceptable medium of the present invention contains the cationic polymer and amine oxide at levels such that the equivalent ratio of cationic groups in the cationic polymer to the moles of amine oxide is at least 2, in some cases at least 3 and in other cases at least 5. Also, the equivalent ratio of cationic groups in the cationic polymer to the moles of amine oxide can be up to 30, in some cases up to 25, in other cases up to 20, in some instances up to 15 and in other instances up to 10. The equivalent ratio is a value where the aqueous gel will have its desired viscosity. The equivalent ratio of cationic groups in the cationic polymer to the moles of amine oxide can be any value or range between any of the values recited above.

In an embodiment of the invention, the Zeta Potential has an absolute value of at least 20 with a Zeta Potential having a value of +20 of higher or −20 or lower.

The component can optionally include a cationic surfactant. The cationic surfactant may be one or more selected from $C_{10}$-$C_{24}$ alkyl quaternary ammonium salts and $C_8$-$C_{25}$ imidazolinium salts. Suitable cationic surfactants can include, but are not limited to, a cationic nitrogenous salt containing one long chain acyclic aliphatic $C_{15}$-$C_{22}$ hydrocarbon group selected from:

(i) acyclic quaternary ammonium salts having the formula:

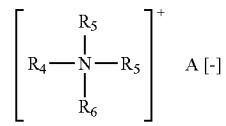

wherein $R_4$ is an acyclic aliphatic $C_{15}$-$C_{22}$ hydrocarbon group, $R_5$ and $R_6$ are $C_1$-$C_4$ saturated alkyl or hydroxyalkyl groups, and A [−] is an anion, especially as described in more detail hereinafter, examples of these surfactants are sold by Sherex Chemical Company under the Adgen trademarks;

(ii) substituted imidazolinium salts having the formula:

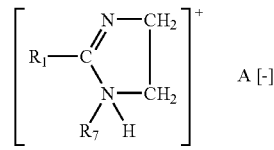

wherein $R_1$ is an acyclic aliphatic $C_{15}$-$C_{21}$ hydrocarbon group, $R_7$ is a hydrogen or a $C_1$-$C_4$ saturated alkyl or hydroxyalkyl group, and A [−] is an anion;

(iii) substituted imidazolinium salts having the formula:

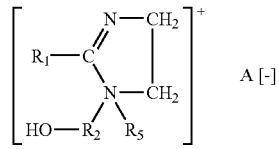

wherein $R_2$ is a divalent $C_1$-$C_3$ alkylene group and $R_1$, $R_5$ and A [−] are as defined above; an example of which is commercially available under the Monaquat ISIES trademark from Mona Industries, Inc.

Another class of cationic surfactants that can be used in the invention is the class of cationic nitrogenous salts having two or more long chain acyclic aliphatic $C_{15}$-$C_{22}$ hydrocarbon groups or one said group and an arylalkyl group are selected from the group consisting of:

(i) acyclic quaternary ammonium salts having the formula:

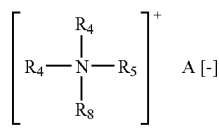

wherein each $R_4$ is an acyclic aliphatic $C_{15}$-$C_{22}$ hydrocarbon group, $R_5$ is a $C_1$-$C_4$ saturated alkyl or hydroxyalkyl group, $R_8$ is selected from the group consisting of $R_4$ and $R_5$ groups, and A [−] is an anion defined as above; examples of which are commercially available from Sherex Company under the Adgen trademarks;

(ii) substituted imidazolinium salts having the formula:

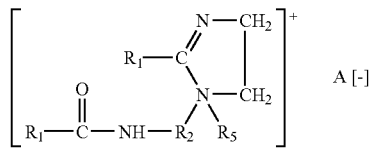

wherein each $R_1$ is an acyclic aliphatic $C_{15}$-$C_{21}$ hydrocarbon group, $R_2$ is a divalent alkylene group having 1 to 3 carbon atoms, and $R_5$ and A [−] are as defined above; examples are commercially available from Sherex Chemical Company under the Varisoft 475 and Varisoft 445 trademarks; and (iii) substituted imidazoliniuxn salts having the formula:

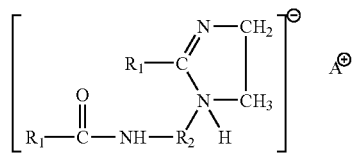

where $R_1$, $R_2$ and A [−] are as defined above; and mixtures thereof.

In an embodiment of the invention, the cationic surfactant is selected from an alkyltrimethylammonium salt, a dialkyldimethylammonium salt, an alkyldimethylbenzylammonium salt, an alkylpyridinium salt, an alkylisoquinolinium salt, benzethonium chloride and an acylamino acid cationic surfactant.

In the cationic nitrogenous salts herein, the anion A [−] provides electrical neutrality. Most often, the anion used to provide electrical neutrality in these salts is a halide such as chloride, bromide or iodide. However, other anions can be used, such as methylsulfate, ethylsulfate, acetate, formate, sulfate, carbonate and the like. Chloride and methylsulfate are preferred herein as anion A.

When used, the amount of cationic surfactant present in the cosmetically acceptable medium is at least 0.05 wt. %, in some cases at least 0.1 wt. % and in other cases at least 0.5 wt. % of the cosmetically acceptable medium. Additionally, the amount present in the cosmetically acceptable medium is up to 5 wt. %, in some cases up to 7.5 wt. % and in other cases up to 10 wt. %. All weight percents are based on the weight of the cosmetically acceptable medium. The amount of cationic surfactant can be any value or range between any of the values recited above.

An optional component of the cosmetically acceptable medium can include a conditioning agent which may be one or more polymers selected from water-soluble poly(meth)acrylates, water-soluble polyamides, water-soluble polyesters, water-soluble polyurethanes, water-soluble poly(vinyl amine), water-soluble poly(ethylene imine), water-soluble amine/epihalohydrin polyamines, water-soluble poly(meth)acrylamide, water-soluble (meth)acrylamide copolymers, water-soluble poly(meth)acrylic acid, water-soluble copolymers of (meth)acrylic acid, poly(diallyl dimethyl ammonium halides), copolymers of diallyl dimethyl ammonium halides, water-soluble vinyl pyrrolidone, water-soluble copolymers of vinyl pyrrolidone, poly(meth)acrylamidopropyltrimethyl ammonium halides, copolymers of (meth)acrylamidopropyltrimethyl ammonium halides, poly(meth)acryloyloxyethyltrimethyl ammonium halides, copolymers of (meth)acryloyloxyethyltrimethyl ammonium halides, poly(meth)acryloyloxyethyltrimethyl ammonium methyl sulfate and copolymers of (meth)acryloyloxyethyltrimethyl ammonium methyl sulfate.

When used, the amount of conditioning agent present in the cosmetically acceptable medium is at least 0.05 wt. %, in some cases at least 0.1 wt. % and in other cases at least 0.5 wt. % of the cosmetically acceptable medium. Additionally, the amount present in the aqueous gel is up to 5 wt. %, in some cases up to 7.5 wt. % and in other cases up to 10 wt. %. All weight percents are based on the weight of the cosmetically acceptable medium. The amount of conditioning agent can be any value or range between any of the values recited above.

Another optional component in the cosmetically acceptable medium includes a water-soluble natural gum. The water-soluble natural gum may comprise one or more selected from xanthan gums, sodium alginates, galactomanans, carageenan and gum arabic. In one embodiment of the invention, the water-soluble natural gum is a quaternary ammonium derivative of hydroxypropyl guar.

The amount of water-soluble natural gum present in the cosmetically acceptable medium is at least 0.05 wt. %, in some cases at least 0.1 wt. % and in other cases at least 0.5 wt. % of the cosmetically acceptable medium. Additionally, the amount present in the cosmetically acceptable medium is up to 2.5 wt. %, in some cases up to 4 wt. % and in other cases up to 5 wt. %. All weight percents are based on the weight of the cosmetically acceptable medium. The amount of water-soluble natural gum can be any value or range between any of the values recited above.

A cellulosic polymer may also be a component of the cosmetically acceptable medium. The cellulosic polymer may be of one or more selected from hydroxyethyl cellulose, hydroxypropyl cellulose, diallyl dimethyl ammonium chloride graft copolymers of hydroxyethylcellulose, polymeric quaternary ammonium salts of hydroxyethyl celluloses reacted with a trimethyl ammonium substituted epoxide and polymeric quaternary ammonium salts of hydroxyethyl celluloses reacted with lauryl dimethyl ammonium substituted epoxides.

The amount of cellulosic polymer present in the cosmetically acceptable medium is at least 0.05 wt. %, in some cases at least 0.1 wt. % and in other cases at least 0.5 wt. % of the cosmetically acceptable medium. Additionally, the amount present in the cosmetically acceptable medium is up to 2.5 wt. %, in some cases up to 4 wt. % and in other cases up to 5 wt. %. All weight percents are based on the weight of the cosmetically acceptable medium. The amount of cellulosic polymer can be any value or range between any of the values recited above.

The composition of the present invention can optionally include a water soluble, ampholytic organic polymer conditioning agent as an essential element. When used, the polymeric ampholytic conditioning agent hereof will generally be present at levels of from about 0.05% to about 10% by weight, in some cases about 0.05% to about 5% and in other cases from about 0.1% to about 4%, with about 0.2% to about 3%, by weight, of the composition in other cases. By "water soluble" ampholytic organic polymer, what is meant is a polymer which is sufficiently soluble in water to form a substantially clear solution to the naked eye at a concentration of 0.1% in water (distilled or equivalent) at 25° C. In one embodiment, the polymer will be sufficiently soluble to form a substantially clear solution at 0.5% concentration, in another embodiment, at 1.0% concentration.

The ampholytic organic polymers useful in the conditioning agent hereof are organic polymers that can provide conditioning benefits to keratin-based substrates such as hair and skin and that are soluble in the composition, particularly in a shampoo composition. Any ampholytic polymers which can provide these benefits can be used regardless of the charge density of the polymer.

In one embodiment, the ampholytic polymer conditioning agent comprises (A) at least one ethylenically unsaturated cationic monomer, (B) at least one ethylenically unsaturated acid containing monomer and (C) about 0 to about 80 mol % of a monomer that is an ethylenically unsaturated nonionic monomer.

The water soluble, organic, ampholytic conditioning agent of the conditioning composition according the present invention can include: (A) about 1 to about 99 mol % of at least one monomer selected from alkyl acrylamidopropyl-dimethyl ammonium halides, alkyl methacrylamidopropyldimethyl ammonium halides, alkyl acryloyloxyethyl dimethyl ammonium halides, alkyl methacryloyloxyethyl dimethyl ammonium halides and dialkyl diallyl ammonium halides; (B) about 1 to about 99 mol % of an ethylenically unsaturated acid containing monomer selected from carboxylic acids and sulfonic acids, in one embodiment at least one monomer is selected from acrylic acid (AA), methacrylic acid (MAA), 2-acrylamido-2-methylpropane sulfonic acid (AMPSA), 2-methacrylamido-2-methylpropane sulfonic acid (MAMPSA), n-methacrylamidopropyl-n,n-dimethylamino acetic acid, n-acrylamidopropyl-n,n-dimethylamino acetic acid, n-methacryloyloxyethyl-n,n-dimethylamino acetic acid and n-acryloyloxyethyl-n,n-dimethylamino acetic acid; and (C) about 0 to about 80 mol % of at least one monomer selected from $C_1$-$C_{22}$ straight or branched chain alkyl acrylate or methacrylate, a $C_1$-$C_{22}$ straight or branched chain n-alkyl acrylamide or methacrylamide, acrylamide, methylacrylamide, n-vinylpyrrolidone, vinyl acetate or ethoxylated and propoxylated acrylate or methacrylate; with a weight average molecular weight of, as determined by viscometry, of at least about 50,000.

The cationic monomers in (A) and the acid functional monomers in (B) can be used in making the cationic polymer described above.

In an embodiment of the invention, the water soluble, organic, ampholytic polymer conditioning agents of the present invention are organic polymers which include: (A) acrylamidopropyltrimethyl ammonium chloride (APTAC), methacrylamidopropyltrimethyl ammonium chloride (MAPTAC), acryloyloxyethyl trimethyl ammonium chloride (AETAC), methacryloyloxyethyl methyl sulfate (METAMS), methacryloyloxyethyl trimethyl ammonium chloride (METAC), or dimethyl diallyl ammonium chloride (DMDAAC); (B) AA, MAA, AMPSA and MAMPSA; and (C) optionally, a $C_1$-$C_{22}$ straight or branched alkyl acrylate or methacrylate such as methyl, ethyl, butyl, octyl, lauryl and stearyl acrylate esters, and methacrylate esters; acrylamide; methacrylamide; a $C_1$-$C_{22}$ straight or branched n-alkyl acrylamide or methacrylamide such as n-methyl, n-ethyl, n-butyl, n-octyl, t-octyl, n-lauryl and n-stearyl acrylamides and methacrylamides.

In an embodiment of the invention, the mol ratio of (A):(B) in the ampholytic polymer ranges from about 20:80 to about 95:5, in another embodiment from about 25:75 to about 75:25. Further, the weight average molecular weight of said polymer, as determined by viscometry, is at least about 50,000, in some cases from about 100,000 to about 10,000,000 and in other cases 150,000 to about 8,000,000. Alternatively, gel permeation chromatography (GPC) using a light scattering detector can be used with approximately the same numbers.

In another embodiment of the invention, the polymers contain at least about 0.1 up to about 20 mol % of the above-defined acrylates, methacrylates, acrylamides, methacrylamides, vinyl acetate, vinyl alcohol and/or n-vinyl pyrrolidone. In a further embodiment, the instant polymers contain about 5 to about 15 mol % of the acrylate, methacrylate, acrylamide, methacrylamide, vinyl acetate, vinyl alcohol and/or n-vinyl pyrrolidone moiety. In a particular embodiment, the polymers contain methyl acrylate and/or acrylamide.

Optionally, the ampholytic polymers additionally contain or are prepared using (C) up to about 80 mol percent, at least about 0.1 mol percent, of a $C_1$-$C_{22}$ straight or branched chain alkyl acrylate or methacrylate; in another embodiment, a $C_1$-$C_{22}$ alkyl acrylate; and in other cases methyl acrylate, a $C_1$-$C_{22}$ straight or branched chain n-alkyl acrylamide or methacrylamide; in another embodiment, a $C_1$-$C_4$ alkyl acrylamide; and in yet another embodiment acrylamide, wherein the upper mol percent of (C) in the instant polymers is limited by solubility considerations. The ampholytic polymer can include about 1 to about 40 mol %, in some cases about 1 to about 35 mol %, of (C), (C) being a monomer that can be selected from $C_1$-$C_{22}$ acrylate esters, $C_1$-$C_{22}$ methacrylate esters, acrylamide and $C_1$-$C_{22}$ n-alkyl acrylamides.

In an embodiment of the invention, the monomers of (C) are selected from (i) $C_1$-$C_{22}$ acrylate esters which are selected from methyl, ethyl, butyl, octyl, lauryl and stearyl acrylate esters; (ii) $C_1$-$C_{22}$ methacrylate esters which are selected from methyl, ethyl, butyl, octyl, lauryl and stearyl methacrylate esters; and (iii) acrylamide, methacrylamide, $C_1$-$C_{22}$ n-alkyl acrylamides which are selected from n-methyl, n-ethyl, n-butyl, n-octyl, t-octyl, n-lauryl and n-stearyl acrylamides and methacrylamides.

The cationic polymers, ampholytic polymers and any other polymers prepared from ethylenically unsaturated monomers can be prepared by conventional solution polymerization techniques or, alternatively, by water-in-oil emulsion polymerization techniques. When prepared as a solution polymerization, the monomer(s) are combined in an aqueous solution and the monomers are polymerized.

In an oil-in-water emulsion system, the monomer(s) are combined in an aqueous solution and dispersed in a suitable hydrocarbon continuous phase to form discrete droplets dispersed within the hydrocarbon. A suitable initiator is then added to the water-in-oil emulsion, which is allowed to polymerize in either an adiabatic or isothermal mode. In an alternative embodiment, an oil soluble monomer can be added after the above-described polymerization step and subsequently polymerized using a suitable initiator to form core-shell dispersed particles.

In an embodiment of the present invention, the polymers are formed via a solution polymerization. To prepare the polymers, the appropriate weights for the desired mol percentages of monomers, as a non-limiting example cationic monomer, sulfonic acid containing anionic monomer, carboxylic acid containing anionic monomer and nonionic monomer are charged to a glass reactor equipped with a stirring means. The desired total monomer concentration can be about 5-50% by weight, in some cases 10-30% by weight. The monomer mixture can then be adjusted to a pH of about 2.0 to about 6.5 with dilute NaOH, heated to a temperature sufficient to initiate polymerization, depending on the particular initiator employed and purged with nitrogen for at least thirty minutes. Polymerization is then initiated by adding an amount of initiator sufficient to polymerize the monomers. The polymerization initiators can include any suitable free radical initiator. After an exotherm is reached, additional dilution water and sodium bisulfite are added to scavenge any residual monomer and to dilute the final product polymer solids.

Any suitable free radical initiator can be used in the present invention. Examples of suitable free radical initiators include, but are not limited to, thermal free radical initiators, photoinitiators and redox initiators. Examples of suitable thermal free radical initiators include, but are not limited to, peroxide compounds, azo compounds and persulfate compounds. A non-limiting example of a suitable redox initiator is the sodium persulfate/sodium bisulfite system.

Examples of suitable peroxide compound initiators include, but are not limited to, hydrogen peroxide, methyl ethyl ketone peroxides, benzoyl peroxides, di-t-butyl peroxide, di-t-amyl peroxide, dicumyl peroxide, diacyl peroxides, decanoyl peroxides, lauroyl peroxides, peroxydicarbonates, peroxyesters, dialkyl peroxides, hydroperoxides, peroxyketals, and mixtures thereof.

Examples of suitable azo compounds include, but are not limited to, 4-4'-azobis(4-cyanovaleric acid), 1-1'-azobis(cyclohexanecarbonitrile), 2-2'-azobisisobutyronitrile, 2-2'-azobis(2-methylpropionamidine)dihydrochloride, 2-2'-azobis(2-methylbutyronitrile), 2-2'-azobis(propionitrile), 2-2'-azobis(2,4-dimethylvaleronitrile), 2-2'-azobis(valeronitrile), 2,2'-azobis[2-methyl-N-(2-hydroxyethyl)propionamide], 4,4'-azobis(4-cyanopentanoic acid), 2,2'-azobis(N,N'-dimethyleneisobutyramidine), 2,2'-azobis(2-amidinopropane)dihydrochloride, 2,2'-azobis(N,N'-dimethyleneisobutyramidine)dihydrochloride and 2-(carbamoylazo)-isobutyronitrile.

Another optional component can be a synthetic non-ionic polymer, which can be added as a component of the cosmetically acceptable medium and may include one or more monomers selected from $C_1$-$C_{22}$ straight or branched chain alkyl or aryl(meth)acrylates, $C_1$-$C_{22}$ straight or branched chain N-alkyl or aryl(meth)acrylamide, (meth)acrylamide, N-methyl(meth)acrylamide, N-vinylpyrrolidone, vinyl acetate, ethoxylated(meth)acrylates, propoxylated (meth)acrylates, hydroxy functional (meth)acrylates, N,N-dimethyl(meth)acrylamide, styrene, $C_1$-$C_{22}$ straight or branched chain alkyl allyl ethers and $C_1$-$C_{22}$ aryl allyl ethers.

The amount of synthetic non-ionic polymer present in the cosmetically acceptable medium is at least 0.05 wt. %, in some cases at least 0.1 wt. % and in other cases at least 0.5 wt. % of the cosmetically acceptable medium. Additionally, the amount present in the cosmetically acceptable medium is up to 5 wt. %, in some cases up to 7.5 wt. % and in other cases up to 10 wt. %. All weight percents are based on the weight of the cosmetically acceptable medium. The amount of synthetic non-ionic polymer can be any value or range between any of the values recited above.

Amino acids may also be added to the composition. Amino acids are organic acids containing both a basic amino group and an acidic carboxyl group. Amino acids are amphoteric and exist in aqueous solution as dipolar ions. Amino acids can be obtained by hydrolysis of a protein or they can be synthesized in various ways, especially by fermentation of glucose.

The amount of amino acid present in the cosmetically acceptable medium is at least 0.05 wt. %, in some cases at least 0.1 wt. % and in other cases at least 0.5 wt. % of the cosmetically acceptable medium. Additionally, the amount present in the cosmetically acceptable medium is up to 5 wt. %, in some cases up to 7.5 wt. % and in other cases up to 10 wt. %. All weight percents are based on the weight of the cosmetically acceptable medium. The amount of amino acid can be any value or range between any of the values recited above.

Proteins may also be used in the composition of the present invention. Proteins are a complex, high polymer containing carbon, hydrogen, oxygen, nitrogen and usually sulfur, and are composed of chains of amino acids connected by peptide linkages. Proteins occur in the cells of all living organisms and in biological fluids. They have many functional forms such as enzymes, hemoglobin, hormones, viruses, genes, antibodies and nucleic acids. They also serve as the basic component of connective tissue (collagen), hair (keratin), nails, feathers, skin, et cetera.

The amount of protein present in the cosmetically acceptable medium is at least 0.05 wt. %, in some cases at least 0.1 wt. % and in other cases at least 0.5 wt. % of the cosmetically acceptable medium. Additionally, the amount present in the cosmetically acceptable medium is up to 5 wt. %, in some cases up to 7.5 wt. % and in other cases up to 10 wt. %. All weight percents are based on the weight of the cosmetically acceptable medium. The amount of protein can be any value or range between any of the values recited above.

The compositions according to the present invention can contain any other ingredient normally used in cosmetics, such as perfumes, dyestuffs, which can serve to color the composition itself or hair fibers, preservatives, sequestering agents, thickeners, silicones, softeners, foam synergistic agents, foam stabilizers, sun filters, peptising agents, and also non-ionic, cationic or amphoteric surface-active agents or mixtures thereof.

The present keratin-treating compositions can also include a variety of non-essential, optional components suitable for rendering such compositions more cosmetically or aesthetically acceptable or to provide them with additional usage benefits. A variety of such are known to those skilled in the art in hair, skin and nail care. These ingredients are well-known and include without limiting the invention thereto: pearlescent aids, such as coated mica, ethylene glycol distearate; opacifiers, such as tin; preservatives, such as 1,2-dibromo-2,4-dicyano butane (MERGUARD® Nalco Chemical Company, Naperville, Ill., USA), benzyl alcohol, 1,3-bis(hydroxymethyl)-5,5-dimethyl-2,3-imidazolidinedione (e.g., GLYDANT®, Lonza Inc., Fairlawn, N.J., USA), methylchloroisothiazolinone (e.g., KATHON®, Rohm & Haas Co., Philadelphia, Pa., USA), methyl paraben, propyl paraben and imidazolidinyl urea; fatty alcohols, such as cetearyl alcohol, cetyl alcohol and stearyl alcohol; sodium chloride; ammonium chloride; sodium sulfate; pH adjusting aids, such as citric acid, sodium citrate, succinic acid, phosphoric acid, monosodium phosphate, disodium phosphate, sodium hydroxide and sodium carbonate; coloring agents or dyes;

perfumes; and sequestering agents, such as disodium ethylenediamine tetra-acetate (EDTA).

The cosmetically acceptable medium of the present invention can also include one or more suitable fragrances. Such fragrances can be included at 0.01% to about 10%, in some cases 0.01% to 5% and in other cases from 0.1% to 5% by weight of the total composition. Numerous fragrances, both natural and synthetic, are well known in the art can be used. Non-limiting examples of suitable fragrances that can be used include those disclosed in Secondini (*Handbook of Perfumes and Flavors*, Chemical Publishing Co., Inc., New York, 1990), incorporated herein by reference, which describes many of the natural and synthetic fragrances used in cosmetics. Suitable natural fragrances include, but are not limited to, jasmines, narcissus, rose, violet, lavender, mint, spice, vanilla, anise, amber, orange, pine, lemon, wintergreen, rosemary, basil and spruce. Suitable synthetic fragrances include, but are no limited to, acetaldehyde, $C_7$ to $C_{16}$ alcohols, benzyl acetate, butyric acid, citric acid, isobutyl phenyl acetate, linalyl butyrate, malic acid, menthol, phenyl ethyl cinnamate, phenyl propyl formate, tannic acid, terpineol, vanillin, amyl salicylate, benzaldehyde, diphenyl ketone, indole, and the like.

Another optional ingredient that can be advantageously used is an anti-static agent. The anti-static agent should not unduly interfere with the in-use performance and end-benefits of the composition. This is more important for shampoo compositions and the anti-static agent should particularly not interfere with the anionic detersive surfactant. Suitable anti-static agents include, for example, tricetyl methyl ammonium chloride. Typically, from about 0.1% to about 5% of such anti-static agent is incorporated into the shampoo compositions.

Though the polymer components may act to thicken the present compositions to some degree, the present compositions may also optionally contain other thickeners and viscosity modifiers, such as an ethanolamide of a long chain fatty acid, such as polyethylene (3) glycol lauramide and coconut monoethanolamide (cocamide MEA), ammonium xylene sulfonate, xanthan gum and hydroxyethyl cellulose.

These optional components generally are used individually in the compositions of the present invention at a level of from about 0.01% to about 10%, typically, from about 0.05% to about 5.0% of the composition.

A method of using the above compositions is also claimed. The compositions of the present invention are utilized conventionally, i.e., the present composition is applied to hair or skin in an effective amount to provide conditioning or styling properties or to deliver another ingredient to the hair or skin, non-limiting examples being a hair dye, peroxide, or a sunscreen or UV protecting agent. The term "effective amount" as used herein, is an amount that is effective in providing the desired conditioning, styling or delivery effect to the keratin substrate. Generally, from about 1 g to about 100 g of the composition is applied depending on the desired purpose.

The compositions hereof can also be useful for cleaning and conditioning the skin. For such applications, the composition would be applied to the skin in a conventional manner, such as by rubbing or massaging the skin with the composition, optionally in the presence of water, and then rinsing it away with water. In the case of non-rinse-off products, the composition is left in full concentration in contact with the skin.

If the compositions are presented in the form of a thickened lotion or a gel, the present composition can form and/or provide the basis for the gel or thickened lotion product. Additional thickeners can be added, such xanthan gums, sodium alginates, gum arabic, cellulose derivatives and/or a mixture of polyethylene glycol stearate or distearate. The concentration of additional thickeners is generally 0.05 to 15% by weight.

In an embodiment of the invention, the inventive compositions include peroxides. When peroxides are included, the composition can be applied to hair to remove color from or bleach the hair to a lighter shade. Further to this embodiment, where appropriate peroxides are used, the composition can be in a dry form, dissolved into water to form a gel and the peroxide added to the resulting gel prior to being applied to the hair.

The present invention will further be described by reference to the following examples. The following examples are merely illustrative of the invention and are not intended to be limiting. Unless otherwise indicated, all percentages are by weight.

EXAMPLES 1-34

Compositions were prepared by combining the ingredients in the table below in a vessel using an overhead mixer at ambient conditions. The surfactants were added to the poly (DADMAC) (PD) in the following order, cocamidopropylbetaine (CAB), lauryl amine oxide (LAMO) and sodium lauryl sulfate (SLS). Viscosity was measured (cps) using a BROOKFIELD® Viscometer (Brookfield Engineering, Stoughton, Mass.) Model RV using an appropriate spindle at 10 rpm and 25° C. The turbidity was determined using a nephelometer providing results in NTU (nephelometer turbidity units). The foaming tendency reflects visual observations. The amount of each component reflects their weight percentage in water.

| Example | PD | CAB | LAMO | SLS | Viscosity | NTU | Foam |
|---|---|---|---|---|---|---|---|
| 1 | 0.5 | 0 | 0 | 0.25 | 10 | 1 | No |
| 2 | 0.5 | 0 | 0.1 | 0.25 | 2850 | 5 | No |
| 3 | 0.5 | 0 | 0.2 | 0.25 | 1100 | 10 | Low |
| 4 | 0.5 | 0.05 | 0 | 0.25 | 450 | 1 | No |
| 5 | 0.5 | 0.05 | 0.1 | 0.25 | 6000 | 5 | No |
| 6 | 0.5 | 0.05 | 0.2 | 0.25 | 600 | 10 | Foam |
| 7 | 0.5 | 0.1 | 0 | 0.25 | 2250 | 105 | No |
| 8 | 0.5 | 0.1 | 0.1 | 0.25 | 6100 | 5 | Some |
| 9 | 0.5 | 0.1 | 0.2 | 0.25 | 150 | 10 | |
| 10 | 0.75 | 0 | 0 | 0.25 | 50 | 1 | No |
| 11 | 0.75 | 0 | 0.1 | 0.25 | 4600 | 5 | Some |
| 12 | 0.75 | 0.05 | 0.1 | 0.25 | 7400 | 5 | Some |
| 13 | 0.75 | 0.1 | 0 | 0.25 | 4600 | 0.1 | |
| 14 | 0.75 | 0.1 | 0.1 | 0.25 | 7600 | 5 | Foam |
| 15 | 0.75 | 0.2 | 0 | 0.25 | 10150 | 0.1 | No |
| 16 | 1 | 0 | 0 | 0.25 | 300 | 1 | Low |
| 17 | 1 | 0.1 | 0 | 0.25 | 6250 | 0.2 | Low |
| 18 | 1 | 0.1 | 0.1 | 0.25 | 7900 | 7 | Foam |
| 19 | 0.2 | 0 | 0.5 | 0.25 | 10 | 9 | Ppt |
| 20 | 0.41 | 0.044 | 0.05 | 0.25 | 350 | 2 | No |
| 21 | .0.41 | 0.044 | 0.05 | 0.25 | 4750 | 0.5 | No |
| 22 | 1.41 | 0.044 | 0.05 | 0.25 | 7100 | 0.1 | No |
| 23 | 0.81 | 0.088 | 0.1 | 0.25 | 5000 | 8 | Foam |
| 24 | 0.81 | 0.088 | 0.1 | 0.25 | 4300 | 8 | Foam |
| 25 | 1.36 | 0.066 | 0.075 | 0.15 | 4250 | 0.3 | V. low |
| 26 | 0.91 | 0.044 | 0.05 | 0.15 | 3200 | 0.1 | V. low |
| 27 | 1.19 | 0.129 | 0.146 | 0.25 | 7000 | 9 | Foam |
| 28 | 1.19 | 0.129 | 0.146 | 0.125 | 150 | 9 | V. foam |
| 29 | 1.3 | 0 | 0 | 0.25 | 650 | 3 | Low |
| 30 | 1.3 | 0 | 0 | 0.125 | 75 | 3 | Low |
| 31 | 1.24 | 0.064 | 0.073 | 0.25 | 8500 | 2 | Low |
| 32 | 1.24 | 0.064 | 0.073 | 0.125 | 2900 | 2 | Low |
| 33 | 1 | 0.2 | 0 | 0.25 | 5000 | 0.2 | Low |
| 34 | 1 | 0.2 | 0 | 0.083 | 400 | 10 | |

The results demonstrate that the gel effect in the present invention occurs when the ratio of cationic polymer to anionic surfactant (sodium lauryl sulfate) is at least 2:1 when an amphoteric surfactant (cocamidopropylbetaine) is present and the effect is amplified when a long chain amine oxide (lauryl amine oxide) is also present.

EXAMPLES 35-51

A first mixture (Mix 1) was prepared by combining 20% poly(DADMAC) with 5% CAB and 0.1% LAMO all on an active weight percent basis of the mixture. Mix 2 was a 38 weight percent solution of SLS. Mix 2 was added to Mix 1 in a vessel equipped with an overhead mixer at ambient conditions. The other component was then added to the mixture. The component mixes were used at the indicated relative weight ratios and the resulting combination of all components was used at the total weight indicated, which is a weight percentage in the resulting aqueous solution. The appearance and viscosity were then recorded (viscosity measured as described above).

| Example | Other Component | Mix 1 (wt. %) | Mix 2 (wt. %) | Other (wt. %) | Total (wt. %) | Appearance | Viscosity (cps) |
|---|---|---|---|---|---|---|---|
| 35 | None | 72 | 28 | 0 | 0.9 | Clear | 4250 |
| 36 | None | 77 | 23 | 0 | 1.1 | Clear | 7300 |
| 37 | Polyquaternium 7[1] | 56 | 22 | 22 | 1.15 | Slight haze | 2100 |
| 38 | OF-420[2] | 56 | 22 | 22 | 1.15 | Hazy | 7300 |
| 39 | Polyquaternium 10[3] | 56 | 22 | 22 | 1.15 | Slight haze | 3050 |
| 40 | PVP K90[4] | 56 | 22 | 22 | 1.15 | Clear | 4600 |
| 41 | OF-420[2] | 0 | 22 | 78 | 1.15 | Polymer separation | |
| 42 | Polyquaternium 28[5] | 56 | 22 | 22 | 1.15 | Clear | 4400 |
| 43 | Polyquaternium 47[6] | 56 | 22 | 22 | 1.15 | Very hazy | 1950 |
| 44 | MACKPRO ® NLP[7] | 56 | 22 | 22 | 1.15 | Slight haze | 4700 |
| 45 | OF-308[8] | 56 | 22 | 22 | 1.15 | Heterogeneous | |
| 46 | HEC[9] | 56 | 22 | 22 | 1.15 | Slight haze | 6000 |
| 47 | OF-420[2] | 0 | 7 | 93 | 0.375 | Polymer separation | |
| 48 | L-Ascorbic Acid | 56 | 22 | 22 | 1.15 | Clear | |
| 49 | Ethanol | 56 | 22 | 22 | 1.15 | Thin | |
| 50 | Propylene Glycol | 56 | 22 | 22 | 1.15 | Thin | |

[1]MERQUAT ® 550 available from NALCO Chemical, Naperville, IL
[2]AETAC/Acrylamide/Acrylic Acid/AMPA copolymer available from WSP Chemicals and Technology, Ambridge, PA
[3]UCARE ® Polymer JR 125 available from Union Carbide Corp., Piscataway, New Jersey
[4]Polyvinylpyrrolidone available from PEAKCHEM, Hangzhou, China
[5]MERQUAT ® 280 available from NALCO Chemical, Naperville, IL
[6]MERQUAT ® 2001 available from NALCO Chemical, Naperville, IL
[7]Quaternium-79 Hydrolyzed Collagen available from McIntyre Group, LTD, University Park, IL
[8]AETAC/Acrylamide/Acrylic Acid copolymer available from WSP Chemicals and Technology, Ambridge, PA
[9]Hydroxyethyl cellulose The results demonstrate that other ingredients can be added to the gel and that the gel maintains its properties with the exception of low molecular weight alcohols and glycols, which tend to negatively impact the gel.

EXAMPLE 52

Wavesetting gel for hair which has been rendered sensitive The gel of example 40 is applied to bleached hair. The hair is set in waves and dried. The hair is hardened and full of life; it feels silky and is easy to comb out.

EXAMPLE 53

The gel of example 43 is applied to bleached hair. The hair is set in waves and dried. The hair is hardened. It is elastic and glossy. It feels silky and is easy to comb out.

EXAMPLE 54

Treatment gel, applied with rinsing 25 ml of the gel of example 38 is left in contact with the hair for 5 minutes after which the hair is rinsed. The hair feels soft and can be combed out easily. The hair is then set in waves and dried. The dry hair can be combed out easily. It is glossy and full of life.

EXAMPLE 55

Treatment gel, applied with rinsing 25 ml of the gel of example 39 is left in contact with the hair for 5 minutes after which the hair is rinsed. The hair feels soft and can be combed out easily. The hair is then set in waves and dried. The dry hair can be combed out easily. It is glossy and full of life.

EXAMPLE 56

The gel of example 43 is applied to hair which has been washed and towelled dry, before setting it in waves. The hair can be combed out easily and feels silky. It is then set in waves and dried. The hair is glossy, full of life, elastic and bulky. It feels silky and is easy to comb out.

EXAMPLE 57

Treatment gel, applied with rinsing 25 ml of the gel of example 36 is left in contact with virgin blond hair, that has just been dyed brown, for 5 minutes after which the hair is rinsed. The hair feels soft and can be combed out easily.

EXAMPLE 58

Treatment gel, applied with rinsing 25 ml of the gel of example 42 is left in contact with ethnic hair, that has just been chemically straightened, for 5 minutes after which the hair is rinsed. The hair feels soft and can be combed out easily.

EXAMPLE 59

Treatment gel, applied with rinsing 25 ml of the gel of example 44 is left in contact with oriental hair, that has just been dyed blond, for 5 minutes after which the hair is rinsed. The hair feels soft and can be combed out easily.

EXAMPLE 60

Treatment gel, applied with rinsing 25 ml of the gel of example 45 is left in contact with ethnic hair, that has just been chemically straightened, for 5 minutes after which the hair is rinsed. The hair feels soft and can be combed out easily.

EXAMPLE 61

Bleaching gel, applied with rinsing A gel according to the invention was prepared as described above, containing on a weight basis 1.5% poly(DADMAC), 0.2% cocamidopropylbetaine, 0.25% sodium lauryl sulfate to which 7.5% hydrogen peroxide was added. The gel had a viscosity, measured as indicated above, of 5,000 cps. The gel was applied to virgin brown hair and remained in contact for 20 minutes, after which time the gel was rinsed away with tap water. The rinsed hair had a bleached blond color after treatment.

The present invention has been described with reference to specific details of particular embodiments thereof. It is not intended that such details be regarded as limitations upon the scope of the invention except insofar as and to the extent that they are included in the accompanying claims.

I claim:

1. A cosmetically acceptable medium comprising one or more components and an aqueous gel comprising water and,
   (a) from 0.1% to 5% by weight based on the water of a cationic polymer that contains at least 50% of repeat units resulting from the polymerization of one or more ethylenically unsaturated monomers that contain a cationic group;
   (b) from 0.05% to 0.5% by weight based on the water of an anionic surfactant having from 8 to 22 carbon atoms, wherein the amount of said anionic surfactant is less than the amount of said cationic polymer;
   (c) from 0.001% to 0.5% by weight based on the water of an amphoteric surfactant, wherein the amount of said amphoteric surfactant is less than the amount of said cationic polymer; and
   (d) up to 0.5% by weight based on the water of a long chain amine oxide, wherein the amount of said long chain amine oxide is less than the amount of said cationic polymer;
   wherein the components include:
   (e) one or more components selected from the group consisting of a fragrance, an oxidizing agent, and a hair dye; and
   (f) one or more optional components selected from the group consisting of a cationic surfactant, a conditioning agent, a synthetic amphoteric polymer, a synthetic ampholytic polymer, a synthetic non-ionic polymer, an amino acid, a protein, dyes, pigments, a cellulosic polymer, one or more vitamins, and mixtures thereof;
   wherein the conditioning agent is selected from the group consisting of water-soluble poly(meth)acrylates, water-soluble polyamides, water-soluble polyesters, water-soluble polyurethanes, water-soluble poly(vinyl amine), water-soluble poly(ethylene imine), water-soluble amine/epihalohydrin polyamines, water-soluble poly(meth)acrylamide, water-soluble (meth)acrylamide copolymers, water-soluble poly(meth)acrylic acid, water-soluble copolymers of (meth)acrylic acid, poly(diallyl dimethyl ammonium halides), copolymers of diallyl dimethyl ammonium halides, water-soluble vinyl pyrrolidone, water-soluble copolymers of vinyl pyrrolidone, poly(meth)acrylamidopropyltrimethyl ammonium halides, copolymers of (meth)acrylamidopropyltrimethyl ammonium halides, poly(meth)acryloyloxyethyltrimethyl ammonium halides, copolymers of (meth)acryloyloxyethyltrimethyl ammonium halides, poly(meth)acryloyloxyethyltrimethyl ammonium methyl sulfate, copolymers of (meth)acryloyloxyethyltrimethyl ammonium methyl sulfate and combinations thereof;
   and wherein the cellulosic polymer is selected from the group consisting of hydroxyethyl cellulose, hydroxypropyl cellulose, and combinations thereof.

2. The cosmetically acceptable medium of claim 1, wherein said amphoteric surfactant comprises a betaine or sultaine surfactant.

3. The cosmetically acceptable medium of claim 1, wherein said amphoteric surfactant comprises cocamidopropyl betaine.

4. The cosmetically acceptable medium of claim 1, wherein said long chain amine oxide comprises lauryl amine oxide and is present in an amount from 0.001% to 2%.

5. The cosmetically acceptable medium of claim 1, further comprising a hydrophobic alcohol, which is a linear or branched alkyl alcohol of the general formula $C_M H_{2M+2}$—N$(OH)_N$, where M is a number from 6-23, and N is 1 when M is 6-12, but where M is 13-23, N may be a number from 1 to 3, said gel including at least one of (a) 0.001% to 5% amine oxide and (b) 0.001% amphoteric surfactant.

6. The cosmetically acceptable medium of claim 5, wherein said alkyl alcohol is a linear monohydric alcohol having from 8-15 carbon atoms.

7. The cosmetically acceptable medium of claim 5, wherein said alkyl alcohol comprises lauryl alcohol.

8. The cosmetically acceptable medium of claim 1, wherein at least 20% of the repeat units of said cationic polymer are derived from dimethyl diallyl ammonium chloride.

9. The cosmetically acceptable medium of claim 1, wherein the amphoteric surfactant is one or more selected from the group consisting of sodium 3-dodecyl-aminopropionate, sodium 3-dodecylaminopropane sulfonate, sodium lauryl sarcosinate, N-alkyltaurines, coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl-yl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine, amidobetaines and amidosulfobetaines.

10. The cosmetically acceptable medium of claim 1, wherein the anionic surfactant is sodium lauryl sulfate or ammonium lauryl sulfate.

11. The cosmetically acceptable medium of claim 1, wherein the one or more vitamins are selected from the group consisting of vitamin A, vitamin E, vitamin D, vitamin E, vitamin B6, vitamin C, vitamin CP, vitamin CG, vitamin D2, vitamin D3, vitamin B 1, vitamin B2, vitamin B3, vitamin B4, vitamin B6, vitamin B 12, vitamin K, beta-carotene, biotin, panthenol, derivatives thereof and combinations thereof.

12. The cosmetically acceptable medium of claim 1, wherein the molecular weight of the cationic polymer is at least 10,000.

13. The cosmetically acceptable medium of claim 1, wherein the cationic polymer comprises residues from one or more monomers selected from the group consisting of diallyl dialkyl ammonium halides, vinyl amine, (meth)acrylamide, vinyl pyrrolidone, (meth)acrylamidopropyltrimethyl ammonium halides, (meth)acryloyloxyethyltrimethyl ammonium halides and (meth)acryloyloxyethyltrimethyl ammonium methyl sulfate.

14. The cosmetically acceptable medium of claim 1, having a viscosity of at least 2000 cps at 23° C.

15. The cosmetically acceptable medium of claim 1, wherein the oxidizing agent is selected from hydrogen peroxide and benzoyl peroxide.

16. The cosmetically acceptable medium of claim 1, wherein the synthetic non-ionic polymer comprises one or more monomers selected from the group consisting of $C_1$-$C_{22}$ straight or branched chain alkyl or aryl(meth)acrylates, $C_1$-$C_{22}$ straight or branched chain N-alkyl or aryl(meth)acrylamide, (meth)acrylamide, N-methyl(meth)acrylamide, N-vinylpyrrolidone, vinyl acetate, ethoxylated (meth)acrylates, propoxylated (meth)acrylates, hydroxy functional (meth)acrylates, N,N-dimethyl(meth)acrylamide, styrene, $C_1$-$C_{22}$ straight or branched chain alkyl allyl ethers and $C_1$-$C_{22}$ aryl allyl ethers.

17. The cosmetically acceptable medium of claim 1, wherein the anionic surfactant is one or more selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfonate, triethanolamine 1-lauryl sulfate, triethanolamine lauryl sulfonate, monoethanolamine cocoyl sulfate, monoethanolamine lauryl sulfonate, sodium tridecyl benzene sulfonate, sodium dodecyl benzene sulfonate, disodium N-octadecyl sulfosuccinamate, tetrasodium N-(1,2-dicarboxyethyl)-N-octadecylsulfos-uc- cinamate, diamyl ester of sodium sulfosuccinic acid, dihexyl ester of sodium sulfosuccinic acid and dioctyl esters of sodium sulfosuccinic acid.

18. The cosmetically acceptable medium of claim 1, wherein the cationic surfactant is one or more selected from the group consisting of $C_{10}$-$C_{24}$ alkyl quaternary ammonium salts and $C_8$-$C_{25}$ imidazolinium salts.

19. The cosmetically acceptable medium of claim 1, wherein the equivalent ratio of cationic groups in the cationic polymer to the amphoteric surfactant is from 2 to 50, the equivalent ratio of cationic groups in the cationic polymer to the anionic surfactant is from 2 to 15, and the cosmetically acceptable medium has a viscosity of at least 2000 cps at 23° C.

20. A method of treating a keratin-based substrate comprising applying to said substrate a cosmetically acceptable medium comprising one or more components and an aqueous gel comprising water and,
  (a) from 0.1% to 5% by weight based on the water of a cationic polymer that contains at least 50% of repeat units resulting from the polymerization of one or more ethylenically unsaturated monomers that contain a cationic group;
  (b) from 0.05% to 0.5% by weight based on the water of an anionic surfactant having from 8 to 22 carbon atoms, wherein the amount of said anionic surfactant is less than the amount of said cationic polymer;
  (c) from 0.001% to 0.5% by weight based on the water of an amphoteric surfactant, wherein the amount of said amphoteric surfactant is less than the amount of said cationic polymer; and
  (d) up to 0.5% by weight based on the water of a long chain amine oxide, wherein the amount of said long chain amine oxide is less than the amount of said cationic polymer;
wherein the components include:
  (e) one or more components selected from the group consisting of a fragrance, an oxidizing agent, and a hair dye; and
  (f) one or more optional components selected from the group consisting of a cationic surfactant, a conditioning agent, a synthetic amphoteric polymer, a synthetic ampholytic polymer, a synthetic non-ionic polymer, an amino acid, a protein, dyes, pigments, a cellulosic polymer, one or more vitamins, and mixtures thereof;
wherein the conditioning agent is selected from the group consisting of water-soluble poly(meth)acrylates, water-soluble polyamides, water-soluble polyesters, water-soluble polyurethanes, water-soluble poly(vinyl amine), water-soluble poly(ethylene imine), water-soluble amine/epihalohydrin polyamines, water-soluble poly(meth)acrylamide, water-soluble (meth)acrylamide copolymers, water-soluble poly(meth)acrylic acid, water-soluble copolymers of (meth)acrylic acid, poly(diallyl dimethyl ammonium halides), copolymers of diallyl dimethyl ammonium halides, water-soluble vinyl pyrrolidone, water-soluble copolymers of vinyl pyrrolidone, poly(meth)acrylamidopropyltrimethyl ammonium halides, copolymers of (meth)acrylamidopropyltrimethyl ammonium halides, poly(meth)acryloyloxyethyltrimethyl ammonium halides, copolymers of (meth)acryloyloxyethyltrimethyl ammonium halides, poly(meth)acryloyloxyethyltrimethyl ammonium methyl sulfate, copolymers of (meth)acryloyloxyethyltrimethyl ammonium methyl sulfate and combinations thereof;
and wherein the cellulosic polymer is selected from the group consisting of hydroxyethyl cellulose, hydroxypropyl cellulose, and combinations thereof.

21. The method according to claim 20, wherein the keratin-based substrate is hair or skin.

22. The method of claim 20, wherein the anionic surfactant is one or more selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine 1 lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, disodium N-octadecyl sulfosuccinamate, tetrasodium N-(1,2-dicarboxyethyl)-N-octadecylsulfos-uc- cinamate, diamyl ester of sodium sulfosuccinic acid, dihexyl ester of sodium sulfosuccinic acid and dioctyl esters of sodium sulfosuccinic acid.

23. The method of claim 20, wherein the amphoteric surfactant is one or more selected from the group consisting of sodium 3-dodecyl-aminopropiona- te, sodium 3-dodecylaminopropane sulfonate, sodium lauryl sarcosinate, N-alkyltaurines, coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl- yl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine, amidobetaines and amidosulfobetaines.

24. The method of claim 20, wherein said amphoteric surfactant comprises a betaine or sultaine surfactant.

25. The method of claim 20, wherein said amphoteric surfactant comprises cocamidopropyl betaine.

26. The method of claim 20, wherein said amine oxide comprises lauryl amine oxide and is present in an amount from 0.001% to 2%.

27. The method of claim 20, wherein said cosmetically acceptable medium further comprises a hydrophobic alcohol, which is a linear or branched alkyl alcohol of the general formula $C_M H_{2M+2}—N(OH)_N$, where M is a number from 6-23, and N is 1 when M is 6-12, but where M is 13-23, N may be a number from 1 to 3, said gel including at least one of (a) 0.001% to 5% amine oxide and (b) 0.001% amphoteric surfactant.

28. The method of claim 27, wherein said alkyl alcohol is a linear monohydric alcohol having from 8-15 carbon atoms.

29. The method of claim 27, wherein said alkyl alcohol comprises lauryl alcohol.

30. The method of claim 20, wherein at least 20% of the repeat units of said cationic polymer are derived from dimethyl diallyl ammonium chloride.

31. The method of claim 20, wherein the anionic surfactant is sodium lauryl sulfate or ammonium lauryl sulfate.

32. The method of claim 20, wherein the one or more vitamins are selected from the group consisting of vitamin A, vitamin E, vitamin D, vitamin E, vitamin B6, vitamin C, vitamin CP, vitamin CG, vitamin D2, vitamin D3, vitamin B1, vitamin B2, vitamin B3, vitamin B4, vitamin B6, vitamin B12, vitamin K, beta-carotene, biotin, panthenol, derivatives thereof and combinations thereof.

33. The method of claim 20, wherein the molecular weight of the cationic polymer is at least 10,000.

34. The method of claim 20, wherein the cationic polymer comprises residues from one or more monomers selected from the group consisting of diallyl dialkyl ammonium halides, vinyl amine, (meth)acrylamide, vinyl pyrrolidone, (meth)acrylamidopropyltrimethyl ammonium halides, (meth)acryloyloxyethyltrimethyl ammonium halides and (meth)acryloyloxyethyltrimethyl ammonium methyl sulfate.

35. The method of claim 20, wherein the oxidizing agent is selected from hydrogen peroxide and benzoyl peroxide.

36. The method of claim 20, wherein the cosmetically acceptable medium has a viscosity of at least 2000 cps at 23° C.

37. The method of claim 20, wherein the synthetic non-ionic polymer comprises one or more monomers selected from the group consisting of $C_1$-$C_{22}$ straight or branched chain alkyl or aryl(meth)acrylates, $C_1$-$C_{22}$ straight or branched chain N-alkyl or aryl (meth)acrylamide, (meth)acrylamide, N-methyl(meth)acrylamide, N-vinylpyrrolidone, vinyl acetate, ethoxylated (meth)acrylates, propoxylated (meth)acrylates, hydroxy functional (meth)acrylates, N,N-dimethyl(meth)acrylamide, styrene, $C_1$-$C_{22}$ straight or branched chain alkyl allyl ethers and $C_1$-$C_{22}$ aryl allyl ethers.

38. The method of claim 20, wherein the cationic surfactant is one or more selected from the group consisting of $C_{10}$-$C_{24}$ alkyl quatemary ammonium salts and $C_8$-$C_{25}$ imidazolinium salts.

39. The method according to claim 20, wherein the cosmetically acceptable medium is selected from the group consisting of an aftershave, a sunscreen, a hand lotion, a shaving cream, a permanent wave, a hair relaxer, a hair bleach, a hair setting composition and a styling gel.

40. The method of claim 20, wherein the equivalent ratio of cationic groups in the cationic polymer to the amphoteric surfactant is from 2 to 50, the equivalent ratio of cationic groups in the cationic polymer to the anionic surfactant is from 2 to 15, and the cosmetically acceptable medium has a viscosity of at least 2000 cps at 23° C.

41. The cosmetically acceptable medium according to claim 1, in dry or powder form capable of being reconstituted into a gel by mixing into water.

42. The cosmetically acceptable medium according to claim 1, wherein the cationic polymer is poly(diallyl dimethyl ammonium chloride).

43. A cosmetically acceptable medium comprising a component and an aqueous gel comprising water and, by weight based on the water,
   from 0.1% to 5% of poly(diallyl dimethyl ammonium chloride) (PDADMAC);
   from 0.05% to 0.5% of an anionic surfactant having from 8 to 22 carbon atoms and including sodium lauryl sulfate, wherein the amount of said anionic surfactant is less than the amount of said PDADMAC;
   from 0.001% to 0.5% of an amphoteric surfactant including cocamidopropylbetaine, wherein the amount of said amphoteric surfactant is less than the amount of said cationic polymer;
   and up to 0.5% of a long chain amine oxide including lauryl amine oxide, wherein the amount of said long chain amine oxide is less than the amount of said cationic polymer;
   wherein said component includes one or more components selected from the group consisting of a fragrance, an oxidizing agent, and a hair dye; and one or more optional components is selected from the group consisting of a cationic surfactant, a conditioning agent, a synthetic amphoteric polymer, a synthetic ampholytic polymer, a synthetic non-ionic polymer, an amino acid, a protein, dyes, pigments, one or more vitamins, and mixtures thereof; and
   wherein the conditioning agent is selected from the group consisting of water-soluble poly(meth)acrylates, water-soluble polyamides, water-soluble polyesters, water-soluble polyurethanes, water-soluble poly(vinyl amine), water-soluble poly(ethylene imine), water-soluble amine/epihalohydrin polyamines, water-soluble poly(meth)acrylamide, water-soluble (meth)acrylamide copolymers, water-soluble poly(meth)acrylic acid, water-soluble copolymers of (meth)acrylic acid, poly (diallyl dimethyl ammonium halides), copolymers of diallyl dimethyl ammonium halides, water-soluble vinyl pyrrolidone, water-soluble copolymers of vinyl pyrrolidone, poly(meth)acrylamidopropyltrimethyl ammonium halides, copolymers of (meth)acrylamidopropyltrimethyl ammonium halides, poly(meth)acryloyloxyethyltrimethyl ammonium halides, copolymers of (meth)acryloyloxyethyltrimethyl ammonium halides, poly(meth)acryloyloxyethyltrimethyl ammonium methyl sulfate, copolymers of (meth)acryloyloxyethyltrimethyl ammonium methyl sulfate and combinations thereof.

* * * * *